US009222111B2

(12) United States Patent
Yoshida et al.

(10) Patent No.: US 9,222,111 B2
(45) Date of Patent: Dec. 29, 2015

(54) METHOD OF PRODUCING LAURIC ACID-CONTAINING OIL OR FAT

(75) Inventors: Hiroshi Yoshida, Cincinnati, OH (US); Fumikazu Takahashi, Tochigi (JP); Yasushi Takimura, Tochigi (JP)

(73) Assignee: Kao Corporation, Tokyo (JP)

( * ) Notice: Subject to any disclaimer, the term of this patent is extended or adjusted under 35 U.S.C. 154(b) by 361 days.

(21) Appl. No.: 13/070,957

(22) Filed: Mar. 24, 2011

(65) Prior Publication Data

US 2012/0245368 A1 Sep. 27, 2012

(51) Int. Cl.
*C11B 1/02* (2006.01)
*C11B 7/00* (2006.01)
*C12P 7/64* (2006.01)
*C11B 1/10* (2006.01)

(52) U.S. Cl.
CPC ... *C12P 7/64* (2013.01); *C11B 1/10* (2013.01); *C11B 7/00* (2013.01); *C12P 7/6409* (2013.01)

(58) Field of Classification Search
None
See application file for complete search history.

(56) References Cited

U.S. PATENT DOCUMENTS

| 8,486,672 | B2 | 7/2013 | Yoshida et al. |
| 2011/0217743 | A1 | 9/2011 | Yoshida et al. |
| 2012/0065415 | A1* | 3/2012 | Greaney et al. ............... 554/21 |
| 2012/0164713 | A1* | 6/2012 | Brown et al. ............. 435/257.2 |

FOREIGN PATENT DOCUMENTS

| JP | 2005-220061 A | 8/2005 |
| WO | WO 2009/103065 A2 | 8/2009 |
| WO | WO 2011/108755 A1 | 9/2011 |

OTHER PUBLICATIONS

Chroomonas diplococca UTEX LB422 strain information (accessed at http://www.straininfo.net/strains/814168/browser).*
Chroomonas mesostigmatica NIES-1370 strain information (accessed at http://mcc.nies.go.jp/strainList.do?strainId=1644).*
Chroomonas nordstedtii NIES-707 strain information (accessed at http://mcc.nies.go.jp/strainList.do?strainId=870).*
Chroomonas nordstedtii NIES-710 strain information (accessed at http://mcc.nies.go.jp/strainList.do?strainId=873).*
Chroomonas placoidea NIES-705 strain information (accessed at http://mcc.nies.go.jp/strainList.do?strainId=866).*
International Search Report (ISR) and Written Opinion (WO) for PCT/JP2012/058505, I.A. fd: Mar. 23, 2012, ISR mailed by the European Patent Office, Rijswijk, Netherlands on Jun. 12, 2012.
Radakovits, R et al., "Genetic engineering of fatty acid chain length in Phaeodactylum tricornutum," Metab Eng 13(1): 89-95 (Jan. 2011), Academic Press, Brugge, Belgium.
International Search Report (ISR) for PCT/JP2011/055434, I.A. fd: Mar. 2, 2011, mailed by the European Patent Office, Rijswijk, Netherlands on Aug. 10, 2011.
Written Opinion of the International Searching Authority for PCT/JP2011/055434, I.D. fd: Mar. 2, 2011, mailed by the European Patent Office, Berlin, Germany on Aug. 10, 2011.
Harland, AD et al, "Distribution of lipids between the zooxanthellae and animal compartment in the symbiotic sea anemone *Anemonia viridis*: wax esters, triglycerides and fatty acids," Marine Biology 110: 13-19 (Feb. 1991), Springer, Berlin, Germany.
Treignier, C et al, "Effect of light and feeding on the fatty acid and sterol composition of zooxanthellae and host tissue isolated from the scleractinian coral *Turbinaria reniformis*," Limnology and Oceanography, 53(6): 2702-2710 (Nov. 2008), American Society of Limnology and Oceanography, Inc., Waco, TX.
Parrish, CC et al, "Time courses of intracellular and extracellular lipid classes in batch cultures of the toxic dinoflagellate, *Gymnodinium* cf. *nagasakiense*," Marine Chemistry 48(a): 71-82 (Dec. 1994), Elsevier, Amsterdam, Netherlands.
Chisti, Y, "Biodiesel from microalgae," Biotechnology Advances 25(3): 294-306 (May 2007), Oxford: Elsevier Science, New York.
Gouveia, L et al., "*Neochloris oleabundans* UTEX #1185: a suitable renewable lipid source for biofuel production," J Ind Microbiol Biotechnol 36(6): 821-826 (Jun. 2009), Houndmills, Great Britain.
Henderson, RJ et al, "Lipid composition and biosynthesis in the marine dinoflagellate *Crypthecodinium cohnii*," Phytochem 27(6): 1679-1683 (1988), Pergamon Press, Great Britain.
Okuyama, H. et al., "Phylogenetic significance of the limited distribution of octadecapentaenoic acid in prymnesiophytes and photosynthetic dinoflagellates," Proc NIPR Symp Polar Biol. 6:21-26 (1993), National Institute of Polar Research, Tokyo, Japan.
Suzuki, M et al., "Isolation of peridinin-related norcarotenoids with cell growth-inhibitory activity from the cultured dinoflagellate of *Symbiodinium* sp., a symbiont of the Okinawan soft coral *Clavularia viridis*, and analysis of fatty acids of the dinoflagellate," Chem. Pharm. Bull 51(6):724-727 (2003), Pharmaceutical Society of Japan, Tokyo, Japan.
Mansour, MP et al., "The fatty acid and sterol composition of five marine dinoflagellates," J. Physiol. 35: 710-720 (1999), Cambridge Univ. Press, Oxford, England.

* cited by examiner

*Primary Examiner* — Lora E Barnhart Driscoll
*Assistant Examiner* — Paul D. Pyla
(74) *Attorney, Agent, or Firm* — Sterne, Kessler, Goldstein & Fox P.L.L.C.

(57) ABSTRACT

To provide a method for supplying lauric acid with algae.
A method for producing an oil or fat containing lauric acid as a constituent fatty acid including: culturing, in a medium, at least one species of algae in the class Cryptophyceae selected from the group consisting of algae belonging to the genus *Rhodomonas* and algae belonging to the genus *Chroomonas* selected from among *Chroomonas diplococca*, *Chroomonas mesostigmatica*, *Chroomonas nordstedtii*, and *Chroomonas placoidea* and recovering, from the culture product, an oil or fat having a lauric acid content of 3 weight % or higher of the fatty acid composition.

15 Claims, No Drawings

METHOD OF PRODUCING LAURIC ACID-CONTAINING OIL OR FAT

FIELD OF THE INVENTION

The present invention relates to a method for producing an oil or fat containing lauric acid as a constituent fatty acid (hereinafter may also be referred to simply as "lauric acid-containing oil or fat"), the method employing algae.

BACKGROUND OF THE INVENTION

Lauric acid is a typical fatty acid contained in a large amount in coconut oil and palm kernel oil and is used as a raw material of a variety of surfactants, in foods, and for other materials.

Currently, the supply source of lauric acid is limited to coconut and palm kernels, which are grown in limited areas in the world. Cultivated lands now allocated to production of such lauric acid sources will be shared competitively with areas for bio-fuel for diesel engines and for food production. Excessive land cultivation for the production of lauric acid sources causes destruction of tropical rain forests.

Therefore, there is demand for creating a technique for supplying lauric acid, which technique does not rely on coconut or palm kernels.

Meanwhile, algae are known to effectively produce an oil or fat, and the productivity per area of the algae is about 10 times that of a plant or the like (Biotechnology Advances, (2007) 25, 294-306). Among algae, dinophyceae *Cryptheco-dinium chonii*, which grows not via photosynthesis but via heterotrophy, is known to be a lauric acid-producing organism and to have high lauric acid content (15.7%/total lipid) (Phytochemistry, (1988) 27, 1679-1683).

From the viewpoints of cost for carbon sources and other factors, more preferred are algae species which can grow via photosynthesis (autotrophy) and have higher lauric acid content. However, among such photoautotrophic algae species, only *Neochloris oleoabundans*, having a lauric acid content of about 1 to 2% at best, is known (J. Ind. Microbiol. Biotechnol. (2009) 36: 821-826), and no algae species has heretofore been known to have higher lauric acid content.

SUMMARY OF THE INVENTION

The present invention relates to a method for producing an oil or fat containing lauric acid as a constituent fatty acid, which method including: culturing, in a medium, at least one species of algae in the class Cryptophyceae selected from the group consisting of algae belonging to the genus *Rhodomonas* and algae belonging to the genus *Chroomonas* selected from among *Chroomonas diplococca, Chroomonas mesostigmatica, Chroomonas nordstedtii*, and *Chroomonas placoidea*; and recovering, from the culture product, an oil or fat having a lauric acid content of 3 weight % or higher of the fatty acid composition.

The present invention also relates to a method for producing lauric acid, which method including separating and recovering lauric acid from the oil or fat.

MODES FOR CARRYING OUT THE INVENTION

The present invention provides a method for supplying lauric acid through employment of algae.

The present inventors have carried out studies on lauric acid-producing organisms, and have found that, among algae in the class of Cryptophyceae, which are photoautotrophic algae, algae belonging to the genus *Rhodomonas* or algae belonging to the genus *Chroomonas* selected from among *Chroomonas diplococca, Chroomonas mesostigmatica, Chroomonas nordstedtii*, and *Chroomonas placoidea* have high lauric acid content, and that an oil or fat containing lauric acid as a constituent fatty acid at high content can be efficiently produced by use of the algae.

According to the method of the present invention, which employs algae that can readily grow, an oil or fat containing lauric acid as a constituent fatty acid at high content can be efficiently produced, without imposing limitation on the cultivated fields for the growth of coconut and palm kernels or competing in the cultivated land with areas for food production, etc. In addition, according to the method of the present invention, destruction of tropical rain forests can be avoided.

The method of the present invention for producing a lauric acid-containing oil or fat includes culturing, in a medium, at least one species of algae in the class Cryptophyceae selected from the group consisting of algae belonging to the genus *Rhodomonas* and algae belonging to the genus *Chroomonas* selected from among *Chroomonas diplococca, Chroomonas mesostigmatica, Chroomonas nordstedtii*, and *Chroomonas placoidea* and recovering, from the culture product, an oil or fat having a lauric acid content of 3 weight % or higher in the fatty acid composition.

The oil or fat has a lauric acid content of 3 weight % or higher of the fatty acid composition. The lauric acid content is preferably 5 to 60 weight %, more preferably 10 to 60 weight %.

The algae in the class Cryptophyceae employed in the present invention may be any algae strains belonging to the genus *Rhodomonas* or to the genus *Chroomonas* selected from among *Chroomonas diplococca, Chroomonas mesostigmatica, Chroomonas nordstedtii*, and *Chroomonas placoidea*, so long as the strains have an ability to produce an oil or fat having a lauric acid content of 3 weight % or higher in the fatty acid composition.

The algae of the present invention may be selected through, for example, the following screening procedure:

i) dispensing a sterilized medium (WA medium (see Table 2) as a fresh water medium or Daigo IMK medium (see Table 3) as a seawater medium) into a culture container;

ii) inoculating an alga strain to the medium and performing stationary culturing at room temperature (22° C. to 24° C.) under illumination (illuminance: about 3,000 lux, illumination for 12 hours and dark for 12 hours);

iii) recovering the produced alga and extracting oil or fat; methyl esterifying the fatty acids; and determining the fatty acid composition, to thereby select an alga strain which can produce a lauric acid-containing oil or fat; and iv) selecting an alga strain having a lauric acid content of 3 weight % or higher based on the total fatty acid in the oil or fat.

As the algae belonging to the genus *Chroomonas*, examples of preferred *Chroomonas diplococca* including *Chroomonas diplococca* strain UTEX LB2422; examples of preferred *Chroomonas mesostigmatica* including *Chroomonas mesostigmatica* strain NIES1370; examples of preferred *Chroomonas nordstedtii* including *Chroomonas nordstedtii* strains NIES707 and NIES710; examples of preferred *Chroomonas placoidea* including *Chroomonas placoidea* strain NIES705 (these strains are available from The culture collection of algae at University of Texas at Austin (UTEX), National Institute for Environmental Studies (NIES), etc.); and strains having virtually the same phycological properties as those of algae strains are mentioned.

As the algae belonging to the genus *Rhodomonas*, *Rhodomonas salina* is preferred, with *Rhodomonas salina*

UTEX1375, *Rhodomonas salina* CCMP272, and strains having virtually the same phycological properties as those of algae strains being more preferred. These strains are available from UTEX and The Provasoli-Guillard National Center for Culture of Marine Phytoplankton (CCMP).

Examples of the strain having virtually the same phycological properties as those of *Chroomonas mesostigmatica* strain NIES1370 include *Chroomonas mesostigmatica* strain TKB-112. Examples of the strain having virtually the same phycological properties as those of *Chroomonas nordstedtii* strain NIES707 include *Chroomonas nordstedtii* strain #00173. Examples of the strain having virtually the same phycological properties as those of *Chroomonas nordstedtii* strain NIES710 include *Chroomonas nordstedtii* strain #00331. Examples of the strain having virtually the same phycological properties as those of *Chroomonas placoidea* strain NIES705 include *Chroomonas placoidea* strain CCAP 978/8.

Examples of the strain having virtually the same phycological properties as those of *Rhodomonas salina* strain CCMP272 include *Rhodomonas salina* strain MeI-023.

The aforementioned algae strains have the following phycological properties. Strains belonging to the same genus as that of the algae strains, and strains having virtually the same mycological properties as those of the algae strains can be identified on the basis of the following properties.

<Phycological Properties of the Class Cryptophyceae>
  i) Containing phycobilin and chlorophyll c
  ii) Chloroplast surrounded by four membranes
  iii) Having nucleomorph
  iv) Having tubular pleuronematic and tubular unilateral flagella
  v) Accumulating α-1,4-starch <Phycological Properties of the Algae Belonging to the Genus *Chroomonas*>
  i) Barrel-form cell with no cingulum
  ii) Having two ejectisomes in a row
  iii) Blue to green chloroplast
  iv) Stigma generally observed centrally in a cell <Phycological Properties of the Algae Belonging to the Genus *Rhodomonas*>
  i) Egg-form cell having a short cingulum
  ii) Red to reddish brown chloroplast with distinct pyrenoid
  iv) Stigma generally observed centrally in a cell <Phycological Properties of *Chroomonas mesostigmatica* Strain NIES1370>
  i) Having a large number of lamellar structures in a chloroplast
  ii) Having one large pyrenoid with a chloroplast <Phycological Properties of *Chroomonas nordstedtii* Strains NIES707 and NIES710>
  i) Having no stigma
  ii) Having phototaxis with respect to light having a wavelength of 450 nm to 650 nm <Phycological Properties of *Chroomonas placoidea* Strain NIES705>
  i) Having ligules at a flagellum bearing <Phycological Properties of *Rhodomonas salina* UTEX1375 and *Rhodomonas salina* CCMP272>
  i) Two flagellua shorter than the cell length arising from a subapical end of the cell
  ii) Short sulcus, gullet with ejectisomes in two rows, reaching to the cell center
  iii) Having one reddish brown to yellowish orange chloroplast, with one pyrenoid being dorsal and surrounded by marked starch sheath The algae of the present invention also encompass mutants of the aforementioned algae strains and strains having virtually the same mycological properties as those of the aforementioned algae strains.

For example, a mutant strain designed so as to produce an oil or fat having a higher lauric acid content as compared with a corresponding wild-type strain is also included in the algae of the present invention.

Furthermore, a gene derived from the algae in the class Cryptophyceae may be employed to produce an oil or fat having a high lauric acid content.

The algae in the class Cryptophyceae of the present invention may be cultured in an appropriate medium prepared from natural or artificial seawater under illumination through a cultivation method generally employed in culturing of microalgae.

The medium which may be employed in the invention is a known medium which contains natural or artificial seawater as a base, and additives such as a nitrogen source, a phosphorus source, a metal salt, and vitamins.

Examples of the nitrogen source include $NaNO_3$, $KNO_3$, $Ca(NO_3)_2$, $NH_4NO_3$, and $(NH_4)_2SO_4$. Examples of the phosphorus source include $K_2HPO_4$, $KH_2PO_4$, $Na_2HPO_4$, $NaH_2PO_4$, and sodium glycerophosphate. Examples of the metal salt include $NaCl$, $KCl$, $CaCl_2$, $MgCl_2$, $Na_2SO_4$, $K_2SO_4$, $MgSO_4$, $Na_2CO_3$, $NaHCO_3$, $Na_2SiO_3$, $H_3BO_3$, $MnCl_2$, $MnSO_4$, $FeCl_3$, $FeSO_4$, $CoCl_2$, $ZnSO_4$, $CuSO_4$, and $Na_2MoO_4$. Examples of the vitamins include biotin, vitamin B12, thiamine-HCl, nicotinic acid, inositol, folic acid, and thymine.

The aforementioned medium may further contain an appropriate additive such as a carbon source or a trace metal, in order to promote production of lauric acid-containing oil or fat.

Examples of preferred media include Daigo IMK medium, f/2 medium, ESM medium, L1 medium, and MNK medium.

Preferably, the pH of the thus-prepared medium is adjusted to fall within a range of 7.0 to 8.0 through addition of an appropriate acid or base, and is sterilized in an autoclave before use.

In culturing, no particular limitation is imposed on the amount of algae inoculated to the culture medium. However, the amount is preferably 1.0 to 10.0% (vol/vol), more preferably 1.0 to 5.0% (vol/vol), with respect to the amount of culturing medium.

No particular limitation is imposed on the culture temperature, so long as the growth of the algae of the present invention is not adversely affected. Generally, the culturing is preferably performed at 10 to 30° C., more preferably 15 to 25° C.

Light irradiation may be performed under any conditions, so long as photosynthesis can be performed. Needless to say, either artificial light or sunlight may be employed.

The illuminance preferably falls within a range of 100 to 50,000 lux, more preferably 300 to 10,000 lux.

The pH during culturing is generally 6.5 to 8.5, preferably 7.0 to 8.0.

Culturing is performed so that an alga is grown in a high density. For example, the culturing period is 7 to 120 days, preferably 7 to 30 days. Any of aeration and agitation culturing, shake culturing, and stationary culturing may be employed.

After completion of culturing, an alga is separated through a customary method such as centrifugation or filtration. The thus-separated alga mass as is, or a broken product thereof obtained through sonication, by means of Dyno Mill or by other means is subjected to solvent extraction with organic solvent such as chloroform, hexane, butanol, methanol, or ethyl acetate, whereby lauric-acid-containing oil or fat can be recovered.

When strain LB2422 is used, 100 g of the dry alga contains a lauric acid-containing oil or fat in an amount of about 3 to about 4 g. That is, the amount of lauric acid-containing oil or fat produced in 1 L of medium reaches about 0.007 to about 0.016 g.

In this case, the oil or fat has a lauric acid content as high as 5.0 to 17.0 weight % of the fatty acid composition. Thus, the amount of produced lauric acid in 1 L of medium is as high as about 0.0004 to about 0.0027 g.

Lauric acid may be separated from the lauric acid-containing oil or fat by transforming the oil or fat into a fatty acid mixture or an ester of a fatty acid through a known method; and recovering high concentration of lauric acid through the urea addition method, cooling separation, HPLC, supercritical liquid chromatography, etc.

EXAMPLES

Example 1

Culturing of Algae and Analysis of Fatty Acid Composition

From the Culture Collection of Algae at University of Texas at Austin (UTEX) and National Institute for Environmental Studies (NIES), the following 9 algae strains belonging to the genus *Chroomonas* were obtained and employed in the experiments.

TABLE 1

Algae strains

| Organization | No. | genus/species |
|---|---|---|
| UTEX | LB 2422 | *Chroomonas diplococca* |
| NIES | 1004 | *Chroomonas coerulea* |
| NIES | 714 | *Chroomonas coerulea* |
| NIES | 704 | *Chroomonas dispersa* |
| NIES | 1370 | *Chroomonas mesostigmatica* |
| NIES | 707 | *Chroomonas nordstedtii* |
| NIES | 710 | *Chroomonas nordstedtii* |
| NIES | 705 | *Chroomonas placoidea* |
| NIES | 2331 | *Chroomonas* sp. |

Culturing of algae was performed in the following methods. C medium (composition, see Table 2) and WA medium (composition, see Table 3) were employed as fresh water media, and f/2 medium (composition, see Table 4) and a commercial medium (Daigo IMK medium, product of Nihon Pharmaceutical Co., Ltd.) (composition, see Table 5) were employed as seawater media.

TABLE 2

Composition of C medium

| | for 1 L |
|---|---|
| $Ca(NO_3)_2 \cdot 4H_2O$ | 150 mg |
| $KNO_3$ | 100 mg |
| $\beta\text{-}Na_2\text{glycerophosphate} \cdot 5H_2O$ | 50 mg |
| $MgSO_4 \cdot 7H_2O$ | 40 mg |
| Vitamin B12 | 0.1 μg |
| Biotin | 0.1 μg |
| Thiamine HCl | 10 μg |
| *PIV metal mixture solution | 3 mL |
| Tris(hydroxymethyl)aminomethane | 500 mg |

TABLE 2-continued

Composition of C medium

| | for 1 L |
|---|---|
| pH | 7.5 |
| $FeCl_3 \cdot 6H_2O$ | 19.6 mg |
| $MnCl_2 \cdot 4H_2O$ | 3.6 mg |
| $ZnSO_4 \cdot 7H_2O$ | 2.2 mg |
| $CoCl_2 \cdot 6H_2O$ | 0.4 mg |
| $Na_2MoO_4 \cdot 2H_2O$ | 0.25 mg |
| $Na_2EDTA \cdot 2H_2O$ | 100 mg |
| Distilled water | 100 mL |

*PIV metal mixture solution

TABLE 3

Composition of WA medium

| | for 1 L |
|---|---|
| $NaNO_3$ | 20 mg |
| $Ca(NO_3)_2 \cdot 4H_2O$ | 60 mg |
| KCl | 10 mg |
| $MgSO_4 \cdot 7H_2O$ | 20 mg |
| $Na_2\text{glyceroPO}_4$ | 10 mg |
| $Na_2EDTA$ | 5 mg |
| $FeCl_3 \cdot 6H_2O$ | 240 μg |
| $H_3BO_3$ | 1 mg |
| $MnCl_2 \cdot 4H_2O$ | 7.2 mg |
| $ZnCl_2$ | 50 μg |
| $CoCl_2 \cdot 6H_2O$ | 20 μg |
| Tris amino | 100 mg |
| Thiamin·HCl | 100 μg |
| Biotin | 10 μg |
| Vitamin B12 | 10 μg |

TABLE 4

Composition of f/2 medium

| | for 1 L |
|---|---|
| $NaNO_3$ | 75 mg |
| $NaH_2PO_4 \cdot 2H_2O$ | 5 mg |
| Vitamin B12 | 135 μg |
| Biotin | 25 μg |
| Thiamine HCl | 1.1 mg |
| $Na_2SiO_3 \cdot 9H_2O$ | 30 mg |
| *f/2 metal mixture solution | 1 mL |
| Artificial sea water | 999 mL |
| $Na_2EDTA \cdot 2H_2O$ | 880 mg |
| $Fe(NH_4)_2(SO_4)_2 \cdot 6H_2O$ | 920 mg |
| $CoSO_4 \cdot 7H_2O$ | 2.8 mg |
| $ZnSO_4 \cdot 7H_2O$ | 4.6 mg |
| $MgSO_4 \cdot H_2O$ | 30.6 mg |
| $CuCl_2 \cdot 2H_2O$ | 1.36 mg |
| $Na_2MoO_4 \cdot 2H_2O$ | 1.46 mg |
| Distilled water | 100 mL |

*f/2 metal mixture solution

TABLE 5

Composition of IMK medium

| | for 1 L |
|---|---|
| $NaNO_3$ | 200 mg |
| $Na_2HPO_4$ | 1.4 mg |
| $K_2HPO_4$ | 5 mg |
| $NH_4Cl$ | 2.68 mg |
| Fe-EDTA | 5.2 mg |
| Mn-EDTA | 332 μg |
| $Na_2$-EDTA | 37.2 mg |

TABLE 5-continued

Composition of IMK medium

| | for 1 L |
|---|---|
| $ZnSO_4 \cdot 7H_2O$ | 23 µg |
| $CoSO_4 \cdot 7H_2O$ | 14 µg |
| $Na_2MoO_4 \cdot 2H_2O$ | 7.3 µg |
| $CuSO_4 \cdot 5H_2O$ | 2.5 µg |
| $H_2SeO_3$ | 1.7 µg |
| $MnCl_2 \cdot 4H_2O$ | 180 µg |
| Thiamin•HCl | 200 µg |
| Biotin | 1.5 µg |
| Vitamin B12 | 1.5 µg |
| Artificial sea water | 35.96 g |

Sterilized culture tubes (16 mm×150 mm) (product of VWR) each plugged with a sponge stopper (60882-167, product of VWR) were used, and a sterilized medium (10 mL/tube) was dispensed to the tubes. Each alga strain (100 µL (in the case of liquid medium) or 1 platinum loop (in the case of solid medium)) was inoculated to a new culture medium. Stationary culturing was performed at room temperature (22° C. to 24° C.) under a fluorescent lamp (illuminance: about 3,000 lux, illumination for 12 hours and dark for 12 hours).

Through centrifugation of the alga culture at 3,000 rpm for 30 minutes, an alga pellet was obtained. The alga pellet was dried at 80° C. for about 3 hours to about 16 hours, to thereby obtain dry alga, and the weight of the dry product was measured. The dry product was suspended in 1% saline (0.5 mL), and 5 mg/mL 7-pentadecanone (10 µL) was added as an internal standard to the suspension. Subsequently, chloroform (0.5 mL) and methanol (1 mL) were added to the suspension, and the mixture was vigorously stirred and then allowed to stand for 30 minutes. Thereafter, chloroform (0.5 mL) and 1.5% KCl (0.5 mL) were added to the mixture and stirred, followed by centrifugation at 3,000 rpm for 15 minutes. The formed chloroform layer (lower layer) was recovered by using a Pasteur pipette.

The thus-prepared lipid fraction (about 500 µL) was treated with nitrogen to dryness, and 0.5 N potassium hydroxide/methanol solution (700 µL) was added to the dried fraction, and then incubated at 80° C. for 30 minutes. Subsequently, 14% boron trifluoride solution (product of SIGMA) (1 mL) was added to the fraction, and then incubated at 80° C. for 20 minutes. Then, hexane (1 mL) and saturated saline (1 mL) were added to the above mixture, and the mixture was allowed to stand at room temperature for 30 minutes. The thus-obtained hexane layer (upper layer) was recovered and analyzed by GC.

The GC analysis was performed under the following conditions: chromatograph, HP 7890A GC-FID (product of Agilent); column, DB-1 ms 30 m×200 µm×0.25 µm (product of J&W scientific); mobile phase, high-purity helium; flow rate, 1 mL/min; and temperature elevation, 100° C. (1 minute), 5° C./min, and 280° C. (20 minutes). As saturated fatty acid controls, the following commercial products (all produced from SIGMA) were purchased and analyzed: methyl laurate (C12), methyl myristate (C14), methyl palmitate (C16), and methyl stearate (C18). As unsaturated fatty acid controls, the following commercial products (all produced from SIGMA) were purchased and analyzed: methyl palmitoleate (C16:1), methyl oleate (C18:1), methyl linoleate (C18:2), methyl linolenate (C18:3), methyl eicosapentaenoate (C20:5), and methyl docosahexaenoate (C22:6). Identification of fatty acids was performed on the basis of coincidence in retention time between the fatty acid analyte and the corresponding standard. Lauric acid was also identified by GC-MS. C16 multi-unsaturated fatty acids were estimated from the GC-MS analytical results and are represented by C16:x (x is 2 or 3, wherein x represents the number of unsaturated bonds in fatty acid). The GC-MS analysis was performed under the following conditions: chromatograph, HP 7890A GC and 5975C MS (products of Agilent); column, DB-1 ms 30 m×200 µm×0.25 µm (product of J&W scientific); mobile phase, high-purity helium; flow rate, 1 mL/min; and temperature elevation, 100° C. (1 minute), 5° C./min, and 280° C. (20 minutes). The amount of a fatty acid ester detected through GC analysis was calculated with reference to the internal standard, and the sum of the amounts of fatty acids was employed as the total fatty acid amount (g). The fatty acid productivity (g/L or mg/L) was obtained by dividing the total fatty acid amount by the volume of culture liquid (L). The value obtained by dividing the amount of each fatty acid by the total amount of the fatty acids and multiplying the ratio by 100 was employed as a fatty acid content (%).

Table 6 shows the fatty acid compositional data of tested algae species.

TABLE 6

Fatty acid composition analysis

| No. | Medium | date | C12:0 | C14:0 | C16:0 | C16:1 | C16:3 | C18:0 | C18:1 | C18:2 | C18:3 | C20:5 | C22:6 | Productivity (mg/L) |
|---|---|---|---|---|---|---|---|---|---|---|---|---|---|---|
| LB 2422 | IMK | 30 | 16.9 | 24.7 | 7.4 | 2.3 | 0.0 | 1.5 | 6.5 | 6.2 | 14.5 | 14.0 | 6.2 | 15.66 |
| 1004 | C | 47 | 0.0 | 0.0 | 29.8 | 0.0 | 0.0 | 11.3 | 0.0 | 10.9 | 33.9 | 14.2 | 0.0 | 5.9 |
| 714 | WA | 47 | 0.0 | 4.6 | 24.4 | 0.0 | 0.0 | 19.9 | 0.0 | 24.5 | 14.7 | 7.3 | 4.7 | 8.2 |
| 714 | C | 47 | 0.0 | 4.8 | 19.9 | 4.0 | 0.0 | 9.8 | 9.8 | 30.7 | 0.0 | 13.4 | 7.7 | 6.0 |
| 704 | IMK | 47 | 0.0 | 0.0 | 35.7 | 0.0 | 0.0 | 9.2 | 7.9 | 5.6 | 20.3 | 13.7 | 7.6 | 8.9 |
| 1370 | IMK | 47 | 9.2 | 8.9 | 21.5 | 0.0 | 0.0 | 10.3 | 15.0 | 18.9 | 6.6 | 9.7 | 0.0 | 7.7 |
| | f/2 | 47 | 11.1 | 9.6 | 27.7 | 0.0 | 0.0 | 8.8 | 0.0 | 20.4 | 3.0 | 14.1 | 5.3 | 10.8 |
| 707 | C | 47 | 6.3 | 10.0 | 20.7 | 9.0 | 6.4 | 10.3 | 6.0 | 18.3 | 6.0 | 7.1 | 0.0 | 7.0 |
| 710 | C | 47 | 6.9 | 0.0 | 21.8 | 0.0 | 0.0 | 5.2 | 0.0 | 30.6 | 0.0 | 25.6 | 10.0 | 7.3 |
| 705 | IMK | 47 | 7.7 | 14.3 | 24.9 | 0.0 | 0.0 | 4.8 | 3.3 | 13.2 | 10.1 | 16.3 | 5.5 | 11.7 |
| 2331 | f/2 | 47 | 4.4 | 6.1 | 27.5 | 0.0 | 0.0 | 7.2 | 8.8 | 6.6 | 26.9 | 12.3 | 0.0 | 11.5 |

Accumulation of lauric acid (≥5% of the total fatty acids) was observed in *Chroomonas diplococca* LB2422 strain, *Chroomonas mesostigmatica* NIES1370 strain, *Chroomonas nordstedtii* NIES707 strain, *Chroomonas nordstedtii* NIES 710 strain, and *Chroomonas placoidea* NIES705 strain. Particularly, in *Chroomonas diplococca* LB2422 strain, a very high-level accumulation of lauric acid (about 17% of the total fatty acids) was observed.

Example 2

Production of Alga Oil Having High Lauric Acid Content

An oil or fat having high lauric acid content was produced in the following manner.

*Chroomonas diplococca* (strain LB2422) was subjected to stationary culturing in culture tubes (16 mm×150 mm, containing IMK medium (10 mL)) at room temperature (22° C. to 24° C.) under illumination (illuminance: about 3,000 lux, illumination for 12 hours and dark for 12 hours) for four weeks, to thereby produce a seed culture liquid. The seed culture liquid was inoculated into IMK medium (100 mL) at 2% (v/v) placed in a 200-mL Erlenmeyer flask, and stationary culturing was performed at room temperature (22° C. to 24° C.) under illumination (illuminance: about 3,000 lux, illumination for 12 hours and dark for 12 hours) for 31 days. The culture liquid was centrifuged at 3,000 rpm for 30 minutes, to thereby recover cells, which were then washed once with 1% (w/v) aqueous sodium chloride solution.

The alga which had been recovered from the culture liquid (100 mL) was dried at 80° C. for about 16 hours, and chloroform (2 mL) and methanol (4 mL) were added to the dried alga. The mixture was vigorously stirred and then allowed to stand for 30 minutes. Thereafter, chloroform (2 mL) and 1.5% KCl (2 mL) were added thereto, and the obtained mixture was stirred. The stirred mixture was centrifuged at 3,000 rpm for 15 minutes, and the chloroform layer (lower layer) was collected by using Pasteur pipette. An aliquot (100 μL) was recovered from the collected chloroform layer and dried to solid through nitrogen gas sprayed thereto. The dried product was dissolved in chloroform (10 μL). An aliquot (1 μL) was sampled from the chloroform solution, and the neutral fat content thereof was determined by means of Iatroscan (product of Mitsubishi Kagaku Iatron, Inc.). As a result, neutral lipid (0.64 mg) was obtained from the culture liquid (100 mL).

Through a methyl esterification method similar to that described in Example 1, an aliquot (500 μL) of the above-collected chloroform layer was analyzed. As a result, the total amount of the fatty acids obtained from the culture liquid (100 mL) was 3.5 mg, and the lauric acid content of the fatty acids was 5.7%. That is, lauric acid (0.2 mg) was recovered from the culture liquid (100 mL).

Example 3

As algae belonging to the genus *Rhodomonas*, *Rhodomonas salina* UTEX1375 and *Rhodomonas salina* CCMP272 were purchased from The culture collection of algae at University of Texas at Austin (UTEX) and The Provasoli-Guillard National Center for Culture of Marine Phytoplankton (CCMP), and these algae strains were tested by using an IMK medium through the method similar to that employed in Example 1. The test procedure of Example 1 was repeated, except that the culture times described in Table 7 were employed. The total fatty acid productivity and the ratio of each fatty acid were determined. The test has revealed that both algae strains had lauric acid contents of 9.4% and 8.8% respectively, which are higher than 3%.

TABLE 7

| | | | | Fatty acid composition analysis | | | | | | | | |
|---|---|---|---|---|---|---|---|---|---|---|---|---|
| | genus/ | | | Fatty acid composition | | | | | | | | productivity |
| No. | species | medium | Week: | C12:0 | C14:0 | C16:0 | C18:0 | C18:1 | C18:2 | C18:3 | C20:5 | (mg/L) |
| UTEX 1375 | *Rhodomonas salina* | IMK | 7.5 | 9.4 | 11.4 | 52.2 | 18.8 | 0.0 | 8.2 | 0.0 | 0.0 | 590 |
| COMP 272 | *Rhodomonas salina* | IMK | 4 | 8.8 | 9.4 | 24.7 | 10.6 | 10.0 | 0.0 | 9.3 | 14.6 | 330 |

The invention claimed is:

1. A method for producing an oil or fat comprising lauric acid as a constituent fatty acid, which method comprises
   culturing in a medium,
   at least one species of algae selected from the group consisting of *Chroomonas diplococca, Chroomonas mesostigmatica, Chroomonas nordstedtii,* and *Chroomonas placoidea;*
   producing a culture product as a result of the culturing; and
   recovering, from the culture product, an oil or fat composition that comprises fatty acids in which the content of lauric acid is 3 weight % or higher of the fatty acids in the composition.

2. The method according to claim 1, wherein the alga is *Chroomonas diplococca* strain UTEX LB2422, *Chroomonas mesostigmatica* strain NIES1370, *Chroomonas nordstedtii* strain NIES707, *Chroomonas nordstedtii* strain NIES710, or *Chroomonas placoidea* strain NIES705.

3. The method according to any one of claims 1 to 2, wherein culturing is performed for 7 to 120 days under light irradiation at an illuminance of 300 to 10,000 lux.

4. The method of claim 1, wherein the method comprises recovering lauric acid from the oil or fat composition.

5. The method of claim 2, wherein the method comprises recovering lauric acid from the oil or fat composition.

6. The method of claim 3, wherein the method comprises recovering lauric acid from the oil or fat composition.

7. The method of claim 1, wherein said algae is *Chroomonas diplococca*.

8. The method of claim 1, wherein said algae is *Chroomonas mesostigmatica*.

9. The method of claim 1, wherein said algae is *Chroomonas nordstedtii*.

10. The method of claim 1, wherein said algae is *Chroomonas placoidea*.

11. The method according to claim 7, wherein the algae is *Chroomonas diplococca* strain UTEX LB2422.

12. The method according to claim 8, wherein the algae is *Chroomonas mesostigmatica* strain NIES1370.

13. The method according to claim 9, wherein the algae is *Chroomonas nordstedtii* strain NIES707.

14. The method according to claim 9, wherein the algae is *Chroomonas nordstedtii* strain NIES710.

15. The method according to claim 10, wherein the algae is *Chroomonas placoidea* strain NIES705.

* * * * *